US00PP34454P2

(12) United States Plant Patent
Beekenkamp

(10) Patent No.: US PP34,454 P2
(45) Date of Patent: Jul. 26, 2022

(54) ***CAMPANULA* PLANT NAMED 'BKPCMPNN'**

(50) Latin Name: *Campanula portenschlagiana*
Varietal Denomination: 'BKPCMPNN'

(71) Applicant: BEEKENKAMP PLANTS B.V., Maasdijk (NL)

(72) Inventor: Annie Cornelia Beekenkamp, Maasdijk (NL)

(73) Assignee: BEEKENKAMP PLANTS B.V., Maasdijk (NL)

( * ) Notice: Subject to any disclaimer, the term of this patent is extended or adjusted under 35 U.S.C. 154(b) by 0 days.

(21) Appl. No.: 17/459,251

(22) Filed: Aug. 27, 2021

(51) Int. Cl.
*A01H 5/02* (2018.01)
*A01H 6/26* (2018.01)

(52) U.S. Cl.
USPC ..... Plt./414
CPC ..... *A01H 6/264* (2018.05)

(58) Field of Classification Search
USPC ..... Plt./414
CPC ..... A01H 6/264
See application file for complete search history.

(56) References Cited

PUBLICATIONS

CPVO Application Consultation for *Campanula* plant named, 'BKPCMPNN', QZ PBR 2021/0687, filed Mar. 8, 2021, downloaded from https://online.plantvarieties.eu/publicConsultationDetails?registerId=20210687&denomination=BKPCMPNN.*

* cited by examiner

*Primary Examiner* — Anne Marie Grunberg
(74) *Attorney, Agent, or Firm* — C. Anne Whealy

(57) ABSTRACT

A new and distinct *Campanula* plant named 'BKPCMPNN', characterized by its compact, upright to spreading and uniformly mounding plant habit; freely branching habit; freely flowering habit; purple-colored flowers; and good container and garden performance.

2 Drawing Sheets

Figure 1:
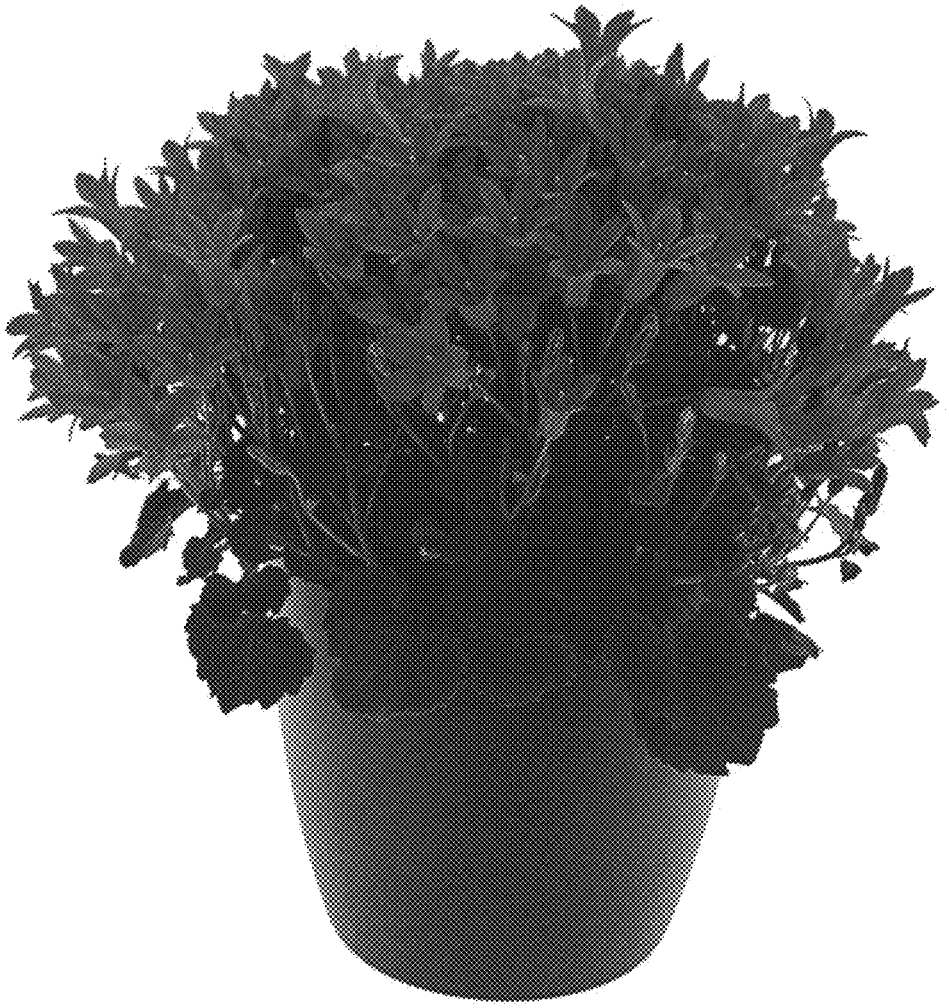

Botanical designation: *Campanula portenschlagiana.*
Cultivar denomination: 'BKPCMPNN'.

PLANT BREEDER'S RIGHTS APPLICATION INFORMATION

An European Community Plant Breeder's Rights application for the instant plant was filed by the Applicant/Assignee, Beekenkamp Plants B.V. of Maasdijk, The Netherlands on Mar. 8, 2021, application number 2021/0687. Foreign priority is not claimed to this application.

BACKGROUND OF THE INVENTION

The present invention relates to a new and distinct *Campanula* plant, botanically known as *Campanula portenschlagiana* and hereinafter referred to by the cultivar name 'BKPCMPNN'.

The new *Campanula* plant is a product of a planned breeding program conducted by the Inventor in Kudelstaart, The Netherlands. The objective of the breeding program is to create new compact and freely-flowering *Campanula* plants with attractive flowers and good garden performance.

The new *Campanula* plant originated from an open-pollination in May, 2018 of *Campanula portenschlagiana* 'Get Mee Purple', not patented, as the female, or seed, parent with an unknown selection of *Campanula portenschlagiana* as the male, or pollen, parent. The new *Campanula* plant was discovered and selected by the Inventor as a single flowering plant from within the progeny of the stated open-pollination grown in a controlled greenhouse environment in Kudelstaart, The Netherlands in May, 2019.

Asexual reproduction of the new *Campanula* plant by terminal vegetative cuttings in a controlled greenhouse environment in Kudelstaart, The Netherlands, since August, 2020, has shown that the unique features of the new *Campanula* plant are stable and reproduced true to type in successive generations.

SUMMARY OF THE INVENTION

Plants of the new *Campanula* plant have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BKPCMPNN'. These characteristics in combination distinguish 'BKPCMPNN' as a new and distinct *Campanula* plant:

1. Compact, upright to spreading and uniformly mounding plant habit.
2. Freely branching habit.
3. Freely flowering habit.
4. Purple-colored flowers.
5. Good container and garden performance.

Plants of the new *Campanula* differ primarily from plants of the female parent, 'Get Mee Purple', in the following characteristics:

1. Leaves of plants of the new *Campanula* are more greyed green in color than leaves of plants of 'Get Mee Purple'.

2. Flowers of plants of the new *Campanula* are positioned above the foliar plane whereas flowers of plants of 'Get Mee Purple' are positioned within and above the foliar plane.

Plants of the new *Campanula* can be compared to plants of *Campanula portenschlagiana* 'Ambella', not patented. In side-by-side comparisons, plants of the new *Campanula* differ primarily from plants of 'Ambella' in the following characteristics:

1. Plants of the new *Campanula* are more compact and narrower than plants of 'Ambella'.
2. Leaves of plants of the new *Campanula* are more greyed green in color than leaves of plants of 'Ambella'.
3. Flowers of plants of the new *Campanula* are positioned above the foliar plane whereas flowers of plants of 'Ambella' are positioned within and above the foliar plane.

BRIEF DESCRIPTION OF THE PHOTOGRAPHS

The accompanying colored photographs illustrate the overall appearance of the new *Campanula* plant showing the colors as true as it is reasonably possible to obtain in colored reproductions of this type. Colors in the photographs may differ slightly from the color values cited in the detailed botanical description which accurately describe the actual colors of the new *Campanula* plant.

The photograph on the first sheet (FIG. 1) is a side perspective view of a typical flowering plant of 'BKPCMPNN' grown in a container.

Figure 2:
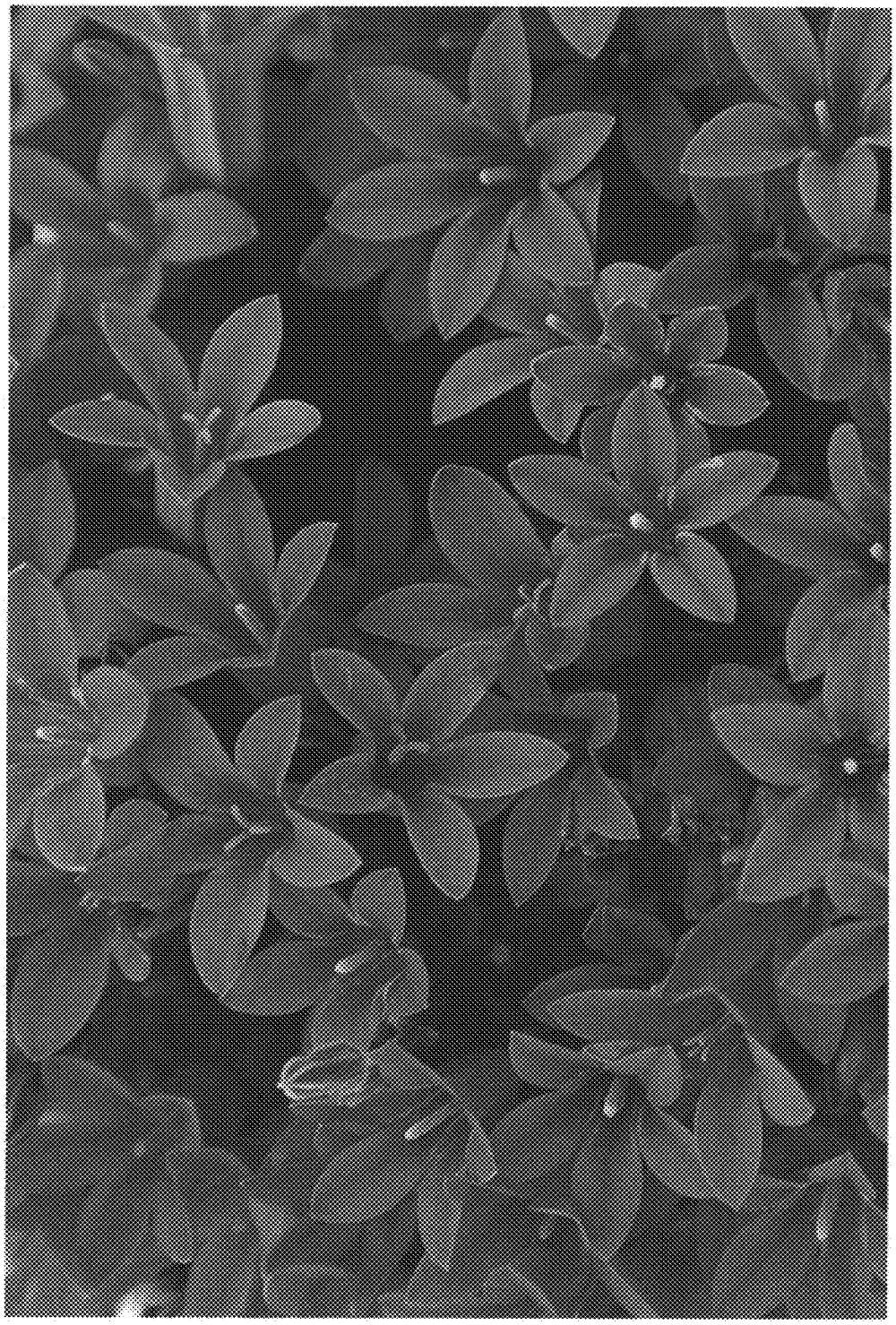

The photograph on the second sheet (FIG. 2) is a close-up view of a typical flowering plant of 'BKPCMPNN'.

DETAILED BOTANICAL DESCRIPTION

Plants used for the aforementioned photographs and following description were grown in 10.5-cm containers during the spring in a heated glass-covered greenhouse in Maasdijk, The Netherlands and under cultural practices typical of commercial *Campanula* production. During the production of the plants, day temperatures ranged from 15° C. to 19° C. and night temperatures ranged from 13° C. to 15° C. Plants were ten weeks from planting rooted young plants when the photographs and description were taken. In the following description, color references are made to The Royal Horticultural Society Colour Chart, 2015 Edition, except where general terms of ordinary dictionary significance are used.

Botanical classification: *Campanula poscharskyana* 'BKPCMPNN'.

Parentage:

*Female, or seed, parent.*—*Campanula portenschlagiana* 'Get Mee Purple', not patented.

*Male, or pollen, parent.*—Unknown selection of *Campanula portenshlagiana*, not patented.

Propagation:

*Type.*—By terminal vegetative cuttings.

*Time to initiate roots, summer and winter.*—About two weeks at temperatures about 18° C.

*Time to produce a rooted young plant, summer and winter.*—About three weeks at temperatures about 19° to 21° C.

*Root description.*—Thin, fibrous; typically white in color, actual color of the roots is dependent on substrate composition, water quality, fertilizers, substrate temperature and physiological age of roots.

*Rooting habit.*—Moderately freely branching; medium density.

Plant description:

*Plant and growth habit.*—Herbaceous perennial; compact, upright to spreading and uniformly mounding plant habit; flattened globular in shape; moderately vigorous growth habit; moderate growth rate; numerous campanulate flowers positioned above the foliar plane.

*Plant height, soil level to top of foliar plane.*—About 9.5 cm.

*Plant height, soil level to top of floral plane.*—About 15.2 cm.

*Plant width.*—About 26.5 cm.

*Lateral branch description.*—Branching habit: Freely branching habit with about 13 primary lateral branches and about seven secondary lateral branches per primary lateral branch developing per plant. Length (excluding flowers): About 9.1 cm. Diameter: About 2 mm. Internode length: About 1.2 cm. Strength: Low; flexible. Aspect: Upright to horizontal. Texture and luster: Smooth, glabrous; glossy. Color, developing: Close to 144B. Color, developed: Close to 144A.

Leaf description:

*Arrangement.*—Alternate, simple.

*Length.*—About 2.1 cm.

*Width.*—About 2.8 cm.

*Shape.*—Reniform.

*Apex.*—Broadly and bluntly acute to obtuse.

*Base, developing leaves.*—Broadly acute.

*Base, developed leaves.*—Hastate.

*Margin.*—Coarsely and irregularly dentate; "teeth" apices are bluntly acute to obtuse.

*Texture and luster, upper and lower surfaces.*—Moderately to densely pubescent; not rugose; matte.

*Venation pattern.*—Pinnate.

*Color.*—Developing leaves, upper surface: Close to 137B. Developing leaves, lower surface: Close to 138A. Fully expanded leaves, upper surface: Close to 137B; venation, close to 137C. Fully expanded leaves, lower surface: Close to a blend of 138B and 191A; venation, close to 146B.

*Petioles.*—Length: About 5 cm. Diameter: About 1 mm by 1.2 mm. Strength: Low; flexible. Texture and luster, upper and lower surfaces: Moderately pubescent; glossy. Color, upper surface: Close to 144B; towards the edges, close to 143A. Color, lower surface: Close to 144B.

Flower description:

*Flower arrangement and flowering habit.*—Single campanulate flowers arranged solitary or in pairs; flowers face mostly upright to slightly outwardly; freely flowering habit with about 650 flowers per plant.

*Natural flowering season.*—Plants begin flowering about ten weeks after planting; relatively long flowering period, plants flower continuously from the spring into the autumn in The Netherlands.

*Flower longevity on the plant.*—About 30 days; flowers persistent.

*Fragrance.*—None detected.

*Flower buds.*—Length: About 1.1 cm. Diameter: About 6 mm. Shape: Oblong. Texture and luster, developing sepals: Moderately pubescent; slightly glossy.

Texture and luster, developing petals: Smooth, glabrous; slightly glossy. Color: Close to 84A; ribs, close to 85D.

*Flower diameter*.—About 2.3 cm.

*Flower depth*.—About 2.1 cm.

*Flower throat diameter*.—About 6 mm.

*Flower tube length*.—About 1.3 cm.

*Flower tube diameter*.—About 7 mm.

*Petals*.—Quantity and arrangement: Typically five, occasionally six, per flower, arranged in a single whorl; lower 56.5% of the petal is fused. Length: About 2.3 cm. Width: About 7 mm. Shape: Oblanceolate; free parts, moderately recurved. Apex: Acute. Margin: Entire; not undulate. Texture and luster, upper surface: Smooth, glabrous; slightly velvety; matte. Texture and luster, lower surface: Smooth, glabrous; matte. Texture and luster, flower throat and tube: Smooth, glabrous; slightly velvety; matte. Color: When opening, upper surface: Close to a blend of N87A and N87B. When opening, lower surface: Close to N87B. Fully opened, upper surface: Close to N87B; venation, close to N87B; color does not change with subsequent development. Fully opened, lower surface: Close to N87C; venation, close to N87A; color does not change with subsequent development. Flower throat: Close to N87B to N87D; venation, close to N87B to N87D. Flower tube: Close to N87C; midvein, close to N87B and lateral venation, close to N87C.

*Sepals*.—Quantity and arrangement: Typically five per flower, arranged in a single whorl. Length: About 5 mm. Width: About 1.25 mm. Shape: Lanceolate. Apex: Narrowly acute. Base: Cuneate. Margin: Entire. Texture and luster, upper surface: Moderately pubescent; moderately glossy. Texture and luster, lower surface: Moderately pubescent; matte. Color: When opening, upper and lower surfaces: Close to 138B. Fully opened, upper surface: Close to a blend of 138B and 143C. Fully opened, lower surface: Close to 143C.

*Peduncles*.—Length: About 7 mm. Diameter: About 1.25 mm. Aspect: Mostly upright. Strength: Low to moderately strong. Texture and luster: Moderately pubescent; moderately glossy. Color: Close to 144A.

*Pedicels* (*flowers in pairs*).—Length: About 2.4 cm. Diameter: About 1 mm. Aspect: Erect to about 45° from peduncle axis. Strength: Low to moderately strong. Texture and luster: Moderately pubescent; moderately glossy. Color: Close to 144A.

*Reproductive organs*.—Stamens: Quantity: Typically five per flower. Filament length: About 6 mm. Filament color: Close to 157D. Anther length: About 6 mm. Anther diameter: About 0.4 mm. Anther shape: Narrowly oblong. Anther color: Close to 11C to 11D. Pollen amount: Moderate. Pollen color: Close to 11D. Pistils: Quantity per flower: One. Pistil length: About 1.3 cm. Style length: About 1.2 cm. Style color: Close to 85B. Stigma diameter: About 4 mm. Stigma shape: Three, four or five-parted, decurrent. Stigma color: Close to 85B. Ovary color: Close to N144A.

*Seeds and fruits*.—To date, seed and fruit development has not been observed on plants of the new *Campanula*.

Pathogen & pest resistance: To date, plants of the new *Campanula* have not been noted to be resistant to pathogens and pests common to *Campanula* plants.

Garden performance: Plants of the new *Campanula* have exhibited good garden performance and to tolerant to rain, wind, temperatures ranging from about 35° C. to about −35° C. and to be suitable for USDA Hardiness Zones 3 to 9.

It is claimed:

1. A new and distinct *Campanula* plant named 'BKPCMPNN' as illustrated and described.

* * * * *